(12) United States Patent
Araki et al.

(10) Patent No.: US 7,348,306 B2
(45) Date of Patent: Mar. 25, 2008

(54) COMPOSITION FOR PROMOTING LACRIMAL SECRETION

(75) Inventors: Hiromasa Araki, Yamatokaoriyama (JP); Atsufumi Kawabata, Yamatokaoriyama (JP); Shuichi Tanaka, Osaka (JP); Kenzo Kawai, Matsubara (JP); Hiroyuki Nishikawa, Kashiba (JP); Sachiyo Nishimura, Sakurai (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 11/211,600

(22) Filed: Aug. 26, 2005

(65) Prior Publication Data

US 2006/0019904 A1 Jan. 26, 2006

Related U.S. Application Data

(62) Division of application No. 10/169,046, filed as application No. PCT/JP00/08687 on Dec. 8, 2000, now abandoned.

(30) Foreign Application Priority Data

Dec. 27, 1999 (JP) ................. 11-369996

(51) Int. Cl.
*A61K 38/00* (2006.01)
(52) U.S. Cl. .......................... 514/2; 530/300
(58) Field of Classification Search ........ None
See application file for complete search history.

(56) References Cited

U.S. PATENT DOCUMENTS 3,910,296 A * 10/1975 Karageozian et al. ........ 134/2
4,745,100 A * 5/1988 Gilbard et al. ............... 514/12
5,629,174 A * 5/1997 Sundelin et al. ........... 435/69.1

FOREIGN PATENT DOCUMENTS

| GB | 1419750 A | 12/1975 |
|----|-----------|---------|
| JP | 62-016429 A | 1/1987 |
| JP | 10-236972 | 9/1998 |

OTHER PUBLICATIONS

Vergnolle et al., PNAS, 1998, vol. 95, pp. 7766-7771.*
Schechter, N.M. et al, "Corneal and Conjunctival Keratinocytes Contain Functional Protease-Activated Receptors," Department of Dermatology, University of Pennsylvania, Philadelphia, Pa.
Nystedt, Sverker et al, "Molecular Cloning of a Potential Proteinase Activated Receptor," *Proc. Natl. Acad. Sci. USA*, vol. 91, Sep. 1994, Medical Sciences, (pp. 9208-9212).
Danjo, Yukitaka et al, "Management of Aqueous-Deficient Dry Eye," vol. 14 (11), 1997 (pp. 1631-1636).
Vergnolle, "Proteinase-activated receptor 2 (PAR-2)-activation peptides: identification of a receptor distinct from PAR-2 that regulates intestinal transport", PNAS. (1998). 95:7766-7771.

* cited by examiner

*Primary Examiner*—Christopher Tate
*Assistant Examiner*—Roy Teller
(74) *Attorney, Agent, or Firm*—Browdy and Neimark, PLLC

(57) ABSTRACT

A composition for promoting lacrimal secretion which can be used safely and effectively in the lacrimal secretion promoting therapy, not in the conventional supplemental therapy of lacrimal fluid components is provided. The composition comprises a component which activates PAR-2. Also, a contact lens which retains and/or contains said composition for promoting lacrimal secretion is provided.

4 Claims, 2 Drawing Sheets

COMPOSITION FOR PROMOTING LACRIMAL SECRETION

CROSS REFERENCE TO APPLICATIONS

The present application is a division of application Ser. No. 10/169,046, nationalized Jun. 27, 2002, now abandoned, which application is the U.S. national stage of PCT/JP00/08687, filed Dec. 8, 2000, the contents of which are herein repeated by reference.

TECHNICAL FIELD

The present invention relates to a composition for promoting lacrimal secretion for treating and/or preventing an ocular disease followed by lowered lacrimal secretion, that are, dry eye, ectocorneal desquamation, corneitis, corneal ulcer, conjunctivitis and the like. Furthermore, the present invention relates to a DDS (drug delivery system) preparation, a percutaneously absorbing preparation, a topical ophthalmic agent (such as eye drops, ophthalmic ointments and the like) and a composition for a contact lens which contain the composition for promoting lacrimal secretion.

BACKGROUND ART

In recent years, dry eye patients have been increased with spread use of contact lenses and increase in use of VDT. Dry eye is a disease exhibiting symptoms such as xerophthalmia, corneal afflux, foreign body feeling, itching feeling and the like, which results in corneal disorders, in principal, due to a lowered lacrimal secretion. In addition, it is said that when dry eye becomes severe, it also causes paropsia and asthenopia.

It is believed that some causes of lowered lacrimal secretion, there are Riley-day syndrome, Shy-Drager syndrome, Sjögren's syndrome, sarcoidosis, amyloidosis, sequela of radiotherapy, lagophthalmos, vitamin A deficiency, Stevens-Johnson syndrome, occular pemphigoid, blepharitis marginal, meibomitis, sequela of intraoccular surgery, contact lens disorder, diabetic ectocorneal disease, VDT-operation, driving over a long period of time and the like.

The lacrimal fluid exists in a border portion where an eyeball contacts with air, and constitutes a thin fluid layer having a thickness of approximately 7 μm which covers an outermost layer of the eyeball. The lacrimal fluid has a three-layered structure, which consists of, from an outer side, an oily layer, an aqueous layer and a mucinous layer, and each layer plays an important role in preventing the eyeball from dryness. The aqueous layer, which occupies most of the lacrimal fluid thickness, is prevented from the decrement by existing between the oily layer and the mucinous layer to maintain the wettability of the eyeball. The oily layer is in principle secreted from a gland existing around an eyelid, which is called meibom gland, and prevents moisture from evaporation by covering throughout the aqueous layer. Accordingly, when the production of the oily layer is reduced due to meibomitis, the aqueous layer becomes apt to evaporate and, thereby, symptom of dry eye is exhibited. The mucinous layer covers a hydrophobic ectocorneal surface to change the surface to hydrophilic and, thereby, has the function of retaining the aqueous layer on an ectocorneal surface.

The lacrimal fluid has various functions in addition to prevention of dry eye. Other functions of the lacrimal fluid include, for example, protection of cornea and conjunctiva, bacteriostatic action, prevention of infection with bacteria, fungus, virus and the like, feeding of oxygen and a variety of nutritions to cornea and removal of a carbon dioxide gas and metabolites therefrom, dilution and removal of harmful stimuli in the case where cornea and conjunctiva injured, transportation of liquid components such as epidermal growth factors which participate in wound healing and the like and hematocyte components such as fibronectin and the like to the injured portion, retainment of cornea and a conjunctival epithelial cell, regulation of wound healing and the like.

At present, various artificial lacrimal fluid-type eye drops have been sold for the purpose of treatment of lowered lacrimal secretion. However, many of them are a preparations comprising inorganic salts and/or metal chelating agents for the purpose of supplementing the lacrimal fluid and, therefore, although they are temporarily effective in solving the dry feeling of eye followed by a lowered lacrimal secretion, the effect is not sustained because they do not affect the lacrimal secretion itself. In addition, it is difficult to persistently remove unpleasantnesses such as foreign body feeling and itching upon wearing the contact lens, or the burning feeling of eye and the like due to dry eye. Furthermore, when those having a lowered amount of oily secretion from meibom gland increase frequency of treatment with eye drops, the dry feeling of the eye becomes stronger due to washing out of the oily and mucinous layers. This attributes to the problem due to a lacrimal fluid components supplementing therapy, but not a lacrimal secretion promoting therapy, which increases lacrimal secretion itself.

Although there is, as the known lacrimal secretion promoting therapy, a method, in which muscarinic drug such as pilocarpine is used as a lacrimal secretion stimulating agent, it has not been a satisfactory preparation yet because of the problems of side effects and the like. Therefore, ophthalmologists and dry eye patients could do nothing but take the lacrimal fluid supplementing therapy while they knew the therapy has only temporal effects.

As stated above, the ophthalmologists and dry eye patients have desired development of a composition for promoting lacrimal secretion which can be used safely and effectively in the lacrimal secretion promoting therapy, not in the conventional lacrimal fluid components supplementing therapy.

On the other hand, it has been known that PAR (Protease-activated receptor) belongs to a G-protein coupled seven transmembrane receptor family and is a receptor which is activated by a protease. (Hollenberg, M. D., Trends Pharmacol. Sci., 17, 3-6, 1996; Hollenberg, M. D., Trends Pharmacol. Sci., 20, 271-273, 1999). PAR is cleaved at a particular N-terminal site of an extracellular domain by a protease to expose a new N-terminal. It is believed that the newly exposed N-terminal becomes a linear ligand and binds to a known active site to activate the receptor (Hollenberg, M. D., Trends Pharmacol. Sci., 17, 3-6, 1996; Hollenberg, M. D., Trends Pharmacol. Sci., 20, 271-273, 1999; Vu, T. K. et al., Cell, 64, 1057-68, 1991).

It has been reported that there are 4 subtypes, PAR-1, PAR-2, PAR-3 and PAR-4 in PAR and that they have different functions from each other. It has been found that PAR-1, PAR-3 and PAR-4 are activated by thrombin (Vu, T. K. et al., Cell, 64, 1057-1063, 1991; Hollenberg, M. D., Trends Pharmacol. Sci., 17, 3-6, 1996; Ishihara, H. et al., Nature, 386, 502-6, 1997; Kahn, M. L. et al., Nature, 394, 690-4, 1998; Xu, W. F. et al., Proc. Natl. Acad. Sci. USA, 95, 6642-6, 1998), and PAR-2 is activated by trypsin (Nystedt, S. et al., Proc. Natl. Acad. Sci. USA, 91, 9208-12, 1994;

Molino, M. et al., J. Biol. Chem., 272, 6011-7, 1997) and tryptase (Molino, M. et al., J. Biol. Chem., 272, 6011-7, 1997; Fox, M. T. et al., FEBS Lett., 417, 267-9, 1997).

A site to be cleaved on the amino acid sequences of PAR-1 (Vu, T. K. et al., Cell, 64, 1057-1063, 1991), PAR-2 (Nystedt, S. et al., Proc. Natl. Acad. Sci. USA, 91, 9208-12, 1994), PAR-3 (Ishihara, H. et al., Nature, 386, 502-6, 1997) and PAR-4 (Kahn, M. L. et al., Nature, 394, 690-4, 1998; Xu, W. F. et al., Proc. Natl. Acad. Sci. USA, 95, 6642-6, 1998) has been known, and it has been also known that PAR-1, PAR-2 and PAR-4 are activated by an exogenous treatment with a synthetic peptide comprising 5-6 amino acids which are synthesized based on an active amino acid sequence at the site to be cleaved (Vu, T. K. et al., Cell, 64, 1057-68, 1991; Nystedt, S. et al., Proc. Natl. Acad. Sci. USA, 91, 9208-12, 1994; Ishihara, H. et al., Nature, 386, 502-6, 1997; Kahn, M. L. et al., Nature, 394, 690-4, 1998; Xu, W. F. et al., Proc. Natl. Acad. Sci. USA, 95, 6642-6, 1998; Dery, O. et al., Am. J. Physiol., 274, C1429-52, 1998).

Activation of inositol 1,4,5-trisphosphate (IP3) and protein kinase C series has been known as one of intracellular signals through PAR-2 (Hollenberg, M. D., Trends Pharmacol. Sci., 20, 271-273, 1999; Dery, O. et al., Am. J. Physiol., 274, C1429-52, 1998; Zheng, X. L. et al., J. Pharmacol. Exp. Ther., 285, 325-34, 1998).

For PAR-2, an inflammatory response (Cirono, G. et al., J. Exp. Med., 183, 821-827, 1996; Kawabata, A. et al., Br. J. Pharmacol., 125, 419-422, 1998), and a constricting and relaxing action in gastric blood vessel and trachea have been reported (Saifeddine, M. et al., Br. J. Pharmacol., 118, 521-531, 1996; Moffatt, J. D. et al., Br. J. Pharmacol., 125, 591-594, 1998; Cocks, T. M. et al., Nature, 398, 156-160, 1999; Hollenberg, M. D. et al., Can. J. Physiol. Pharmacol., 75, 832-884, 1997). In addition, it has been reported that PAR-2 is expressed in prostate, small intestine, colon, liver, kidney and pancreas (Stephan, K. B. et al., Biochem. J., 341, 1009-1016, 1996). However, PAR-2 relating to the lacrimal secretion has not been reported yet, and the present inventors have first demonstrated that a component which activates PAR-2 (that is, an agonist) possesses the lacrimal secretion promoting action.

OBJECT OF THE INVENTION

The present invention was done in light of the above prior art, and an object of the present invention is to provide a safe and effective composition for promoting lacrimal secretion. That is, the object of the present invention is to provide a composition possessing the novel lacrimal secretion promoting action, which can solve a problem of side effects caused by conventional artificial lacrimal fluid-type eye drops aiming at supplement of lacrimal fluid components, and lacrimal secretory stimulating agents such as muscarinic drugs or the like.

This and other objects as well as advantages of the present invention will be illustrated below by referring to accompanying drawings.

SUMMARY OF THE INVENTION

Figure 1:
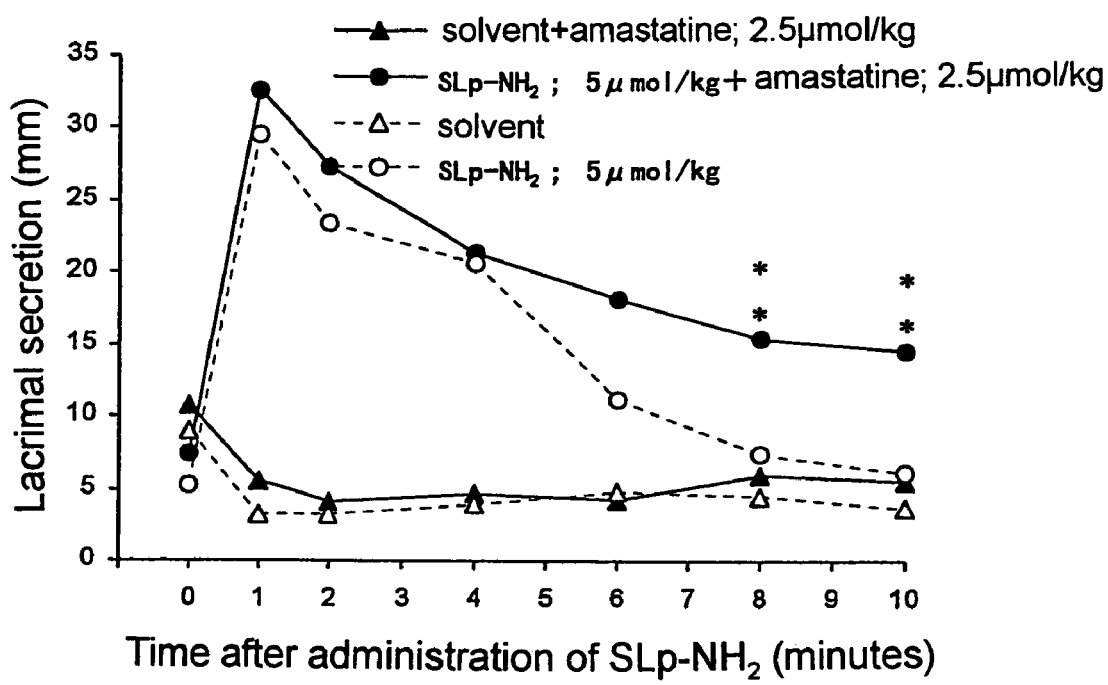
FIG. 1 is a graph illustrating the activity of PAR-2 agonist peptide on the rat lacrimal secretion in vivo. **P<0.01 vs SLp-NH$_2$ (Tukey test).

The present inventors have investigated for the purpose of developing a preferable drug for a composition for promoting lacrimal secretion and, as the result, found that the lacrimal secretion is caused by a component which activates PAR-2, which resulted in completion of the present invention.

That is, the present invention provides:

(1) A composition for promoting lacrimal secretion comprising a component which activates a PAR-2 receptor;

(2) The composition for promoting lacrimal secretion according to (1), wherein the component is a peptide;

(3) The composition for promoting lacrimal secretion according to (2), wherein the peptide comprises a sequence selected from the group consisting of Ser-Leu-Ile-Gly-Arg-Leu-NH$_2$ (SEQ ID NO:1), Ser-Leu-Ile-Gly-Arg-Leu-OH (SEQ ID NO:2), and trans-cinnamoyl-Leu-Ile-Gly-Arg-Leu-ornithine-NH$_2$ (SEQ ID NO: 3);

(4) The composition for promoting lacrimal secretion according to (1), wherein the component is a protein;

(5) The composition for promoting lacrimal secretion according to (4), wherein the protein is trypsin and/or tryptase;

(6) The composition for promoting lacrimal secretion according to any one of (1)-(5), wherein a substance which inhibits inactivation or degradation of the component is used together and/or incorporated therein;

(7) The composition for promoting lacrimal secretion according to (6), wherein the substance is a peptidase inhibitor;

(8) The composition for promoting lacrimal secretion according to (7), wherein the peptidase inhibitor is amastatine;

(9) The composition for promoting lacrimal secretion according to any one of (1)-(8), which is formulated into a drug delivery system (SDS) preparation;

(10) The composition for promoting lacrimal secretion according to any one of (1)-(9), which is formulated into a percutaneously absorbing preparation;

(11) The composition for promoting lacrimal secretion according to any one of (1)-(9), which is an ophthalmic composition;

(12) The composition for promoting lacrimal secretion according to (11), wherein the ophthalmic composition has the form of a washing solution, an eye drop, an ophthalmic ointment, or an ophthalmic gel;

(13) The composition for promoting lacrimal secretion according to (11), wherein the ophthalmic composition has the form of an eye drop for contact lens, a preserving solution for contact lens or a washing solution for contact lens;

(14) A contact lens which retains and/or contains the composition for promoting lacrimal secretion according to any one of (1)-(8);

(15) The contact lens according to (14), which retains and/or contains the composition for promoting lacrimal secretion according to any one of (1)-(8) so that it is sustainedly released;

(16) An agent for treating or preventing an ocular disease, which comprises the composition for promoting lacrimal secretion according to any one of (1)-(8);

(17) The agent for treating or preventing an ocular disease according to (16), wherein the ocular disease is dry eye, ectocorneal desquamation, corneitis, corneal ulcer or conjunctivitis.

DETAILED DESCRIPTION OF THE INVENTION

The phrase "a component which activates PAR-2" refers to any substance, which is naturally occurring or artificially synthesized, possessing the ability to activate PAR-2 and, includes, for example, a peptide, a protein, other compounds and the like. Particularly, the component which activates PAR-2 includes, for example, trypsin and tryptase, that are naturally occurring proteins which activate PAR-2; the Ser-Phe-Leu-Leu-Arg-NH$_2$ peptide (SEQ ID NO:4) which is synthesized based on the previously reported amino acid sequence of human PAR-1 (Vu, T. K. et al., Cell, 64(6), 1057-1068, 1991) and which is known to have the agonist activity for human PAR-1 (Hollenberg, M. D., Molec. Pharmacol., 43, 921-930, 1993) and the weak agonist activity for PAR-2 (Kawabata, A. et al., J. Pharmacol. Exp. Ther., 288, 358-70, 1999) (hereinafter referred to as "SFp-NH$_2$"); the Ser-Leu-Ile-Gly-Arg-Leu-NH$_2$ peptide (SEQ ID NO:1) which is synthesized based on the previously reported amino acid sequence of rat PAR-2 (Saifeddine, M. et al., Br. J. Pharmacol., 118(3), 521-530, 1996) and which is known to have the agonist activity for rat PAR-2 (Hollenberg, M. D., Trends Pharmacol. Sci., 17, 3-6, 1996; Nystedt, S. et al., Proc. Natl. Acad. Sci. USA, 91, 9208-12, 1994) (hereinafter referred to as "SLp-NH$_2$"); the Ser-Leu-Ile-Gly-Arg-Leu-OH peptide (SEQ ID NO:2) which is SLp-NH$_2$ wherein the C-terminal is not amidated (hereinafter referred to as "SLp-OH"); and the trans-cynnamoyl-Leu-Ile-Gly-Arg-Leu-ornithine-NH$_2$ peptide (SEQ ID NO:3) which is reported to specifically activate PAR-2 (hereinafter referred to as "tcLp-NH$_2$") (Hollenberg, M. D. et al., Can. J. Physiol. Pharmacol., 75, 832-41, 1997) and the like. Furthermore, an antibody against PAR-2 or a fragment thereof may be a protein or a peptide which specifically activates PAR-2.

In addition, the component which activates PAR-2 may be obtained by screening various substances for the ability to activate PAR-2 according to any known method. For example, a substance which binds to PAR-2 may be screened by directly detecting interaction between PAR-2 and the substance to be tested using labeling with a radioisotope, surface plasmon resonance and the like. In addition, a substance which induces signal transmission through PAR-2 may be screened using an index of the biological activity caused by activation of PAR-2 in a cell or tissue expressing PAR-2. In addition, a substance which exhibits the lacrimal secretion promoting action can be screened by using the following method for measurement of an amount of lacrimal fluid. For example, an assay method for PAR-2 activation is described in Hollenberg, M. D., Can. J. Physiol. Pharmacol., 75, 832-841, 1997 and Kawabata, A., J. Pharmacol., Exp. Ther., 288, 358-370, 1999. The method for screening a substance which binds to a receptor to induce an action (that is an agonist) has been well known in the art (see, for example, Hollenberg, M. D., Trends Pharmacol. Sci., 20, 271-273, 1999, Dery, O., Am. J. Physiol., 274, C1429-C1452, 1998, Kawabata, A., J. Pharmacol. Exp. Ther., 288, 358-370, 1990).

The term "peptide" used herein refers to an oligopeptide and a relatively short polypeptide. The peptide contains, for example, 2-40 amino acid residues, preferably 3-20 amino acid residues, and more preferably 5-15 amino acid residues. The peptide may be naturally created or chemically synthesized. The peptide may be synthesized according to the known method, for example, such as that described in Carpino, L. A. et al., J. Org. Chem., 37, 3404-3409, 1972. Also, the peptide may be produced by using the recombinant DNA technique. In addition, the peptide may contain a modified or non-natural amino acid residue.

An amount of lacrimal fluid may be measured according to the known method such as a method of Iga et al. using a rat (Iga, Y. et al., Jpn. J. Pharmacol., 78, 373-80, 1998). In particular, a rat is anesthetized with pentobarbital (50 mg/kg, intraabdominal administration), and a paper with 2 mm width for testing the human lacrimal secretion function, the Schirmer test paper (Showa Yakuhin Kako Co., Ltd.) is inserted into a lower eyelid of the rat. After a period of time fixed has passed, the test paper is removed, and a length of the wetted portion of the test paper is measured using a caliper square. If a statistically significant increase of lacrimal secretion is observed when a test substance is administered, it can be said that the substance possesses the lacrimal secretion promoting activity.

The composition for promoting lacrimal secretion of the present invention is a composition comprising the component which activates PAR-2, and is useful as an agent for treatment or prevention of ocular diseases such as dry eye, ectocorneal desquamation, corneitis, corneal ulcer, conjunctivitis and the like, which can be treated or prevented by promoting the lacrimal secretion. When the composition is used as the treating or preventing agent, the composition for promoting lacrimal secretion of the present invention can be used as such or can be used after various treatments such as dilution with water and the like thereto. Also, the composition for promoting lacrimal secretion can be used by incorporation in a drug or a quasi-drug, particularly in a composition for eye drops, a percutaneously absorbing preparation or the like. An amount of the agent for promoting lacrimal secretion to be incorporated may be appropriately selected depending on a product, but may be usually 0.001-50% by weight, and particularly 0.01-10% by weight in the case of a systemic administration preparation. When the amount is below 0.001% by weight, there is a possibility that the satisfactory lacrimal secretion promoting activity is not observed. On the other hand, when the amount exceeds 50% by weight, there is a possibility that properties of the product itself such as the stability, the flavoring property and the like are deteriorated.

The component which activates PAR-2, which is contained in the composition for promoting lacrimal secretion of the present invention, may be contained in the preparation as a pharmaceutically acceptable salt thereof. The pharmaceutically acceptable salt includes, for example, salts with bases such as an inorganic base and an organic base, and acid addition salts with acids such as an inorganic acid, an organic acid and a basic or acidic amino acid and the like. The inorganic base includes, for example, alkali metals such as sodium, potassium and the like, alkaline-earth metals such as calcium, magnesium and the like, and aluminum, ammonium and the like. The organic base includes, for example, primary amines such as ethanolamine and the like, secondary amines such as diethylamine, diethanolamine, dicyclohexylamine and N,N'-dibenzylethylenediamine and the like, tertiary amines such as trimethylamine, triethylamine, pyridine, picoline, triethanolamine and the like, and the like. The inorganic acid includes, for example, hydrochloric acid, hydrobromic acid, nitric acid, sulfuric acid, phosphoric acid and the like. The organic acid includes, for example, formic acid, acetic acid, lactic acid, trifluoroacetic acid, fumaric acid, oxalic acid, tartaric acid, maleic acid, benzoic acid, citric acid, succinic acid, malic acid, methanesulfonic acid, ethanesulfonic acid, benzenesulfonic acid, p-toluenesulfonic acid and the like. The basic amino acid includes, for example, arginine, lysine, ornithine and the like. The acidic amino acid includes, for example, aspartic acid, glutamic acid and the like.

When the peptide or protein is used as the component which activates PAR-2, the durability of the activity of PAR-2 activation can be enhanced by using together with a drug such as amastatine, a peptidase inhibitor, or by incorporating amastatine into the composition, because the peptide and protein are degraded by a peptidase existing in a living body. When the component is not the peptide, those skilled in the art can identify the substance which inactivates or degrades the component, select another substance which inhibits the substance, and use the selected substance together or incorporated it in the composition.

As a mode of administrating a pharmaceutical composition of the present invention, oral, topical ocular, intravenous, transmucosal, transdermal, intramuscular, subcutaneous, or rectal administration or the like can be properly selected, and the pharmaceutical composition of the present invention can be formulated into various preparations depending on the mode of the administration. Although each preparation is described below, a dosage form used in the present invention is not limited thereto, and the composition of the present invention can be used as various kinds of preparations which are ordinarily used in the field of pharmaceutical preparation.

Systemic Administration Preparation

When the composition of the present invention is used as a drug for treating the lowered lacrimal secretion, an oral dosage of the component which activates PAR-2 is preferably in a range of 3-300 mg/kg, and more preferably in a range of 10-100 mg/kg. When the systemic administration of the composition of the present invention is conducted, particularly when it is intravenously administered, the component should be administered such that the effective blood concentration thereof becomes in a range of 2-200 µg/mL, more preferably in a range of 5-100 µg/mL, although it may vary depending on sex, age and body type of the subject.

When the drug is orally administered, the dosage form of the drug can be properly selected from the group consisting of powders, granules, capsules, pills, tablets, elixirs, suspensions, emulsions, syrups and the like. In addition, modification such as sustained-releasing, stabilizing, easy-disintegrating, hard-disintegrating, enterally solubilizing, and easy-absorbing properties and the like may be applied to such the preparation depending on the purpose. The dosage form in the case of the oral administration includes, for example, chew, sublingual, buccal, lozenges, ointments, attaching preparations, solution and the like, and it can be properly selected therefrom. In addition, modification such as sustained-releasing, stabilizing, easy-disintegrating, hard-disintegrating, enterally solubilizing, and easy-absorbing properties and the like may be applied to such the preparation.

Known drug delivery system (DDS) techniques can be adopted to each dosage form as described above. The term DDS preparation herein refers to a preparation having an optimal form in light of an administration route, bioavailability, side effect or the like, such as a sustained-releasing preparation, a topically applying preparation (such as a lozenge, a buccal tablet, a sublingual tablet and the like), a controlled-releasing preparation, an enteric preparation, a gastric-soluble preparation and the like.

Basically, as constituents of DDS, there are a drug, a drug-releasing module, a film, and a therapeutic program. Particularly, for each constituent, the drug has preferably a short half-life such that the blood concentration of the drug is quickly lowered when the releasing thereof is stopped, the film is preferably not reactive with a biological tissue at the administered portion, and the therapeutic program preferably maintains the excellent drug concentration during a predetermined period. Basically, the drug-releasing module has a drug reservoir, a release-controlling portion, an energy source and a releasing port or a releasing surface. These basic constituents may not be all supplemented at the same time, and some of them may be optionally added or omitted to select the excellent form of DDS.

The material to be used for DDS includes polymers, cyclodextrin derivatives, lecithin and the like. The polymers include an insoluble-polymer (silicone, ethylene-vinyl acetate copolymer, ethylene-vinyl alcohol copolymer, ethyl cellulose, cellulose acetate and the like), a water-soluble polymer and a hydroxylgel-forming polymer (polyacrylamide, a cross-linked polyhydroxyethyl methacrylate polymer, a cross-linked polyacrylic polymer, polyvinyl alcohol, polyethylene oxide, a water-soluble cellulose derivative, cross-linked poloxamer, chitin, chitosan and the like), a gradually-dissolving polymer (ethyl cellulose, partial ester of methyl vinyl ether-malic anhydride copolymer and the like), a gastric-soluble polymer (hydroxypropylmethyl cellulose, hydroxypropyl cellulose, carmellose sodium, macrogol, polyvinyl pyrrolidone, dimethylaminoethyl methacrylate-methyl methacrylate copolymer and the like), enteric polymer (hydroxypropylmethyl cellulose phthalate, cellulose acetate phthalate, hydroxypropylmethyl cellulose acetate succinate, carboxymethylethyl cellulose, acrylates polymer and the like), and a bio-degradable polymer (thermocoagulated- or -cross-linked albumin, cross-linked gelatin, collagen, fibrin, polycyanoacrylate, polyglycolic acid, polylactic acid, poly-β-hydroxyacetic acid, polycaprolactone and the like), and may be properly selected depending on the dosage form.

Particularly, silicone, ethylene-vinyl acetate copolymer, ethylene-vinyl alcohol copolymer, and partial ester of methyl vinyl ether-maleic anhydride copolymer may be used for controlling release of a drug, cellulose acetate may be used as a material of an osmotic pump, ethyl cellulose, hydroxypropylmethyl cellulose, hydroxypropyl cellulose and methyl cellulose may be used as a film raw material of the sustained-release preparation, and the cross-linked polyacryl polymer may be used as an adsorbing agent to oral or ophthalmic mucosa.

In addition, the preparation can be produced by adding additives such as solvents, excipients, coating agents, bases, binding agents, lubricants, disintegrating agents, solution adjuvants, suspending agents, thickening agents, emulsifying agents, stabilizing agents, buffering agents, isotonicity adjusting agents, soothing agents, preservatives, corrigents, flavors, coloring agents and the like thereto depending on the dosage form thereof (known dosage form such as oral preparation, injections, suppository, percutaneously absorbing preparation and the like).

Each of these additives is specifically exemplified below, but is not limited thereto.

Solvents: purified water, water for injection, physiological saline solution, peanut oil, ethanol, glycerin, Excipients: starches, lactose, dextrose, white sugar, crystalline cellulose, calcium sulfate, calcium carbonate, talc, titanium oxide, trehalose, xylitol, Coating agents: white sugar, gelatin, cellulose acetate phthalate and polymers as described above, Bases: vaseline, vegetable oils, macrogol, oil-in-water emulsion base, water-in-oil emulsion base, Binding agents: starch and derivatives thereof, cellulose and derivatives thereof, naturally-occurring polymer compounds such as gelatin, sodium alginate, tragacanth, gum arabic and the like, synthetic polymer compounds such as polyvinyl pyrrolidone and the like, dextrin, and hydroxypropylated starch, Lubricants: stearic acid and salts thereof, talc, waxes, wheat starch, macrogol, hydrogenated vegetable oils, sucrose fatty acid ester, polyethylene glycol, Disintegrating agents: starch and derivatives thereof, agar, gelatin powder, sodium hydrogen carbonate, cellulose and derivatives thereof, carmellose calcium, hydroxypropyl starch, carboxymethyl cellulose and salts thereof as well as cross-linked polymers thereof, low-substituted hydroxypropyl cellulose, Solution adjuvants: cyclodextrin, ethanol, propylene glycol, polyethylene glycol, Suspending agents: gum arabic, tragacanth, sodium alginate, aluminum monostearate, citric acid, various surfactants, Thickening agents: carmellose sodium, polyvinyl pyrrolidone, methyl cellulose, hydroxypropylmethyl cellulose, polyvinyl alcohol, tragacanth, gum arabic, sodium alginate, Emulsifying agents: gum arabic, cholesterol, tragacanth, methyl cellulose, various surfactants, lecithin, Stabilizing agents: sodium hydrogen sulfite, ascorbic acid, tocopherol, chelating agents, inert gas, reducing substances, Buffering agents: sodium hydrogenphosphate, sodium acetate, boric acid, Isotonicity adjusting agents: sodium chloride, glucose, Soothing agents: procaine hydrochloride, lidocaine, benzyl alcohol, Preservatives: benzoic acid and salts thereof, paraoxybenzoic acid esters, chlorobutanol, invert soap, benzyl alcohol, phenol, thimerosal, Corrigents: white sugar, saccharin, licorice extract, sorbitol, xylitol, glycerin, Flavors: bitter tincture, rose oil, Coloring agents: water-soluble edible pigment, lake pigment.

As described above, effects such as the sustained effective blood concentration of a drug, enhancement of bioavailability and the like can be expected by formulating a pharmaceutical into a DDS preparation such as a sustained-releasing preparation, an enteric preparation, a drug controlled-releasing preparation and the like. However, there is a possibility that the component which activates PAR-2 is inactivated or degraded in a living body and, as the result, the desired effect is lowered or disappear. For example, when the component which activates PAR-2 is a peptide, it is known that many of such the peptides are degraded by aminopeptidase in a living body (Godin, D. et al., Eur. J. Pharmacol., 253, 225-30, 1994). Accordingly, a substance, which inhibits a substance which inactivates or degrades the component which activates PAR-2 (for example, a substance which inhibits aminopeptidase), may be used together with the composition for promoting lacrimal secretion of the present invention to further sustain the effects of the component.

Amastatine, Arphamenine A, Arphamenine B, and bestatin and the like are known as an aminopeptidase inhibitor. These compounds may be incorporated in the preparation, or may be administered apart from the preparation. When the above component is not a peptide, those skilled in the art can properly identify a substance which inactivates or degrades the component, select another substance which inhibits the substance, and can incorporated the substance in the preparation or use together with the preparation.

Ingredients other than those described above, which are used in the conventional composition as an additive, may be used in the preparation. An amount of these ingredients to be added may be a usual amount without deteriorating the effect of the present invention.

The composition for promoting lacrimal secretion of the present invention can be also applied to the skin. A preparation to be applied to the skin is not particularly limited to, but includes lotions, creams, gels, ointments, paste, plaster, attaching preparations, patch, cataplasm, tape, TTS (Transdermal Therapeutic System) preparations and the like. An application site is not particularly limited to, but includes breast, nether parts, regions of back, leg, cheek, eyelid, lower eyelid, arm, neck and the like. A percutaneously absorbing preparation herein refers to all the preparations as described above in a broader sense, but refers to a preparation having a support such as plaster, attaching preparations, patch, cataplasm, tape, TTS preparations and the like in a narrower sense.

Particularly, a sticky polymer which is used for the percutaneously absorbing preparation having a support includes acrylic series, rubber series, silicone series and the like, but is not particularly limited thereto so long as it is biologically acceptable.

As the acrylic series, although (co)polymers containing alkyl (meth)acrylate as a main component may be suitably used, copolymers of alkyl (meth)acrylate and a monomer which is copolymerizable with said alkyl (meth)acrylate may be used. A ratio of alkyl (meth)acrylate in the constituents of (co)polymers containing alkyl (meth)acrylate as a main component is preferably equal to or higher than 20% by weight.

Alkyl (meth)acrylate includes methyl acrylate, butyl acrylate, isobutyl acrylate, hexyl acrylate, octyl acrylate, 2-ethylhexyl acrylate, isooctyl acrylate, decyl acrylate, isodecyl acrylate, lauryl acrylate, stearyl acrylate, methyl methacrylate, butyl methacrylate, isobutyl methacrylate, 2-ethylhexyl methacrylate, isooctyl methacrylate, decyl methacrylate, isodecyl methacrylate, lauryl methacrylate, stearyl methacrylate and the like, and they may be used alone or in combination thereof.

The polymerizable monomer as described above is preferably a functional monomer such as a monomer containing an alkoxy group having an ether linkage on a side chain, a monomer having a hydroxy group, a monomer having a carboxyl group, a monomer having an amido group, a monomer having an amino group, a monomer having a sulfoxyl group, a monomer having an alkoxy group, a monomer having a nitrogen-containing heterocycle and the like. Embodiments of such the monomer are described below.

The monomer containing an alkoxy group having an ether linkage on a side chain includes, for example, methoxyethyl (meth)acrylate, ethoxydiethyl (meth)acrylate, methoxydiethyleneglycol (meth)acrylate, methoxypropylene glycol (meth)acrylate and the like.

The monomer having a hydroxy group includes, for example, hydroxyalkyl (meth)acrylates such as hydroxyethyl (meth)acrylate, hydroxypropyl (meth)acrylate and the like.

The monomer having a carboxyl group includes, for example, α,β-unsaturated carboxylic acids such as (meth)acrylic acid and the like, monoalkyl maleates such as butyl maleate and the like, maleic acid (anhydride), itaconic acid, fumaric acid, crotonic acid and the like.

The monomer having an amido group includes, for example, alkyl (meth)acrylamides such as (meth)acrylamide, dimethyl (meth)acrylamide, N-butylacrylamide, diethylacrylamide and the like, N-alkoxy (methyl)acrylamides such as butoxymethylacrylamide, ethoxymethylacrylamide and the like, and the like.

The monomer having an amino group includes, for example, dimethylaminoacrylate and the like.

The monomer having a sulfoxyl group includes, for example, styrenesulfonic acid, acrylsulfonic acid, sulfopropyl (meth)acrylate, (meth)acryloyloxynaphthalenesulfonic acid, acrylamidemethylpropanesulfonic acid and the like.

The monomer having an alkoxy group includes, for example, methoxyethyl (meth)acrylate, tetrahydrofurfuryl (meth)acrylate, methoxyethyleneglycol (meth)acrylate, methoxypolyethyleneglycol (meth)acrylate and the like.

The monomer having a nitrogen-containing heterocycle includes, for example, vinylpyrrolidone, methyl vinylpyrrolidone, vinylpiperazine, vinylimidazole and the like.

In addition to the monomers as described above, monomers such as vinyl chloride, vinyl acetate, vinyl propionate, styrene, $\alpha$-methylstyrene, acrylonitrile, ethylene, propylene, butadiene and the like may be used.

The (co)polymer containing alkyl (meth)acrylate as a main component as described above is usually prepared by conducting solution polymerization, in which the monomer as described above is contained in the presence of a polymerization initiator. In the case where solution polymerization is conducted, a solvent for polymerization such as ethyl acetate and the like may be added to a predetermined amount of various monomers, and the mixture may be reacted, under the nitrogen atmosphere, at 50-90° C. for 5-100 hours in a reaction vessel equipped with a stirrer and a condenser in the presence of a polymerization initiator such as azobis- and peroxide-compounds and the like.

The organic solvent for polymerization includes, for example, benzene, ethylbenzene, butylbenzene, toluene, xylene, hexane, heptane, ethyl acetate, hydroxyethyl acetate, methyl benzoate, acetone, methyl cellosolve, ethyleneglycol monoethyl ether, methyl alcohol, propyl alcohol and the like. The azobis polymerization initiator includes 2,2-azobis-iso-butyronitrile, 1,1'-azobis(cyclohexane-1-carbonitrile), 2,2'-azobis(2,4-dimethylvaleronitrile) and the like, and the peroxide polymerization initiator includes, for example, lauroyl peroxide, benzoyl peroxide and the like.

As the rubber series pressure-sensitive adhesive as described above, for example, natural rubber, isoprene rubber, polyisobutylene, polyvinyl ether, polyurethane, polyisoprene, polybutadiene, styrene-butadiene copolymer, styrene-isoprene copolymer, styrene-isoprene-styrene block copolymer and the like may be used.

As the silicone series pressure-sensitive adhesive as described above, for example, silicone rubber such as of polyorgano-siloxane and the like may be used.

In addition, as the pressure-sensitive adhesive, those generally used for preparing a percutaneously absorbing preparation, such as described in JP-A 9-208605, JP-A 10-94595, JP-A 10-94596, JP-A 10-298068 and the like may be used.

A layer of the pressure-sensitive adhesive as described above may be formed on a sheet- or tape-shaped support. As the support, those in which an amount of the percutaneously absorbing drug contained in a layer of the pressure-sensitive adhesive is not lowered due to the loss of the drug through a backside of the support, that is, those comprised of a drug non-permeable material may be suitably utilized.

As the support, films such as of nylon, polyvinyl chloride, plasticized polyvinyl chloride, polyvinylidene chloride, polyethylene, polyethylene terephthalate, polypropylene, cellulose acetate, ethyl cellulose, plasticized vinyl acetate-vinyl chloride copolymer, ethylene-vinyl acetate copolymer, ethylene-ethyl acrylate copolymer and polyurethane, a polyester/polyethylene-vinyl acetate copolymer laminate, a polyethylene-vinyl acetate copolymer/rayon nonwoven fabric laminate, a polyester nonwoven fabric/polyester film laminate, a vinylon nonwoven fabric/polyester film laminate (particularly, see JP-A 10-310521) and films such as of an aluminum sheet and the like may be used, and these materials may be as a single layer or a laminate comprised of two or more thereof. A thickness of the support is preferably equal to or smaller than 2000 µm, and more preferably 2-300 µm.

The composition for promoting lacrimal secretion of the present invention may be contained in finely-divided polymer particles dispersed in a layer of the pressure-sensitive adhesive. The finely-divided polymer particle is, for example, of cross-linked polyvinyl pyrrolidone, cross-linked cellulose, polystyrene, styrene-divinylbenzene copolymer or the like, and the material of the finely-divided polymer particle is properly selected depending on a kind of a drug and the like. A diameter of the finely-divided polymer particle is preferably equal to or smaller than 200 µm, and more preferably equal to or smaller than 50 µm. The drug contained in the finely-divided polymer particle may be existed in the solubilized or non-solubilized state. The solvent to be used for incorporating a drug in the finely-divided polymer particle may be properly selected depending on a kind of a drug or finely-divided polymer particle, and examples thereof include ethyl acetate, toluene, tetrahydrofuran and the like.

In preparation of the percutaneously absorbing preparation of the present invention, conventional methods for producing a pressure-sensitive adhesive tape can be applied for forming a layer of the pressure-sensitive adhesive, such as a solvent coating method, a hot-melt coating method, an electron radiation curing emulsion coating method and the like.

In the solvent coating method as described above, a layer of the pressure-sensitive adhesive having a predetermined thickness can be formed on a support by dissolving or dispersing a pressure-sensitive adhesive, a drug and, if necessary, other additive in a suitable solvent, coating the resulting solution or dispersion on the surface of the support, and then drying the solvent to remove. Alternatively, a layer of the pressure-sensitive adhesive may be prepared by coating the solution or dispersion as described above on a release paper and adhering the resulting layer of the pressure-sensitive adhesive on the surface of a support after drying. If necessary, the percutaneously absorbing preparation in which a finely-divided polymer particle containing a drug is dispersed in a layer of the pressure-sensitive adhesive can be obtained by using a finely-divided polymer particle containing a drug in advance. The solvent to be used includes, for example, benzyl alcohol, butyl benzoate, isopropyl myristate, octanol, propylene glycol, polypropylene glycol, ethylene glycol and the like.

Alternatively, the solution or dispersion as described above may be applied to a release paper on which a silicone resin or the like is coated, and the release paper is dried and adhered to a support, without directly applying the solution or dispersion to the surface of the support. The release paper may be used for protecting the surface of a layer of the pressure-sensitive adhesive of the percutaneously absorbing preparation such as of tape and the like until use. For example, a release paper in which the surface of a polyethylene terephthalate film is treated with silicone may be used.

The thickness of the release paper is preferably equal to or smaller than 1000 μm, and more preferably 10-300 μm.

The thickness of a layer of the pressure-sensitive adhesive may vary depending on an object of use and an application site and, when the thickness becomes small, the adhering force thereof becomes weak, and the content of drug per unit area of the percutaneously absorbing preparation becomes insufficient. On the other hand, when the thickness becomes large, there is a possibility that a drug-releasing rate is lowered since a drug contained in a layer of the pressure-sensitive adhesive near a support does not sufficiently diffuse. Specifically, a layer of the pressure-sensitive adhesive is prepared such that it has a thickness of preferably 3-1000 μm, and more preferably 10-500 μm. In addition, a crosslinking treatment may be applied to a layer of the pressure-sensitive adhesive.

If necessary, additives such as plasticizer, absorption-promoting agent, skin torpent, antioxidant and the like may be added to a layer of the pressure-sensitive adhesive. An amount of the additive to be used varies depending on the kind of additive and is preferably 1-50% by weight, and more preferably 1-10% by weight based on the total weight of the layer of the pressure-sensitive adhesive. When the amount of the additive to be used is smaller than 1% by weight, the adhering force-lowering action becomes small. On the other hand, when the amount exceeds 50% by weight, there is a possibility that the adhering force to a skin becomes too weak, and pressure-sensitive adhesive transfer is caused due to lowering of cohesion or the like.

A placticizer can regulate an adhering force of a layer of the pressure-sensitive adhesive to the skin and reduce irritation upon peeling off from the skin. The plasticizer includes, for example, diisopropyl adipate, phthalic acid ester, diethyl sebacate, higher fatty acid esters, a softening agent described in JP-A 10-179711 and the like.

An absorption-promoting agent includes a compound which enhances the solubility or the dispersibility of a drug in a layer of the pressure-sensitive adhesive, a compound which changes a water-retaining ability of keratin, a keratin-softening ability, a keratin-permeability, or the like, a compound which acts as a carrier and the like.

The compound which enhances the solubility or the dispersibility includes glycols such as ethylene glycol, diethylene glycol, propylene glycol, triethylene glycol, polyethylene glycol, polypropylene glycol and the like, oils and fats such as olive oil, caster oil, squalene, lanolin and the like. The compounds which change the water-retaining ability of keratin, the keratin-softening ability, the keratin-permeability include 1-dodecylazocycloheptane-2-one, oleic acid, isopropyl myristate, middle-chain fatty acid monoglyceride, monoterpenes, 1-menthol, d-limonene urea, allantoin, salicylic acid, methyloctyl sulfoxide, dimethyllaurylamide, dodecylpyrrolidone, iso-sorbitol, dimethylacetamide, dimethyl sulfoxide, dimethylformamide and the like. The compound which acts as a carrier includes, for example, ethanol, iso-propanol, N-methyl-2-pyrrolidone, propylene glycol and the like. In addition, benzyl nicotinate, which is a hair pore opening agent, dibutylhydroxytoluene, which is an antioxidant, and the like may be used. The additive or synergistic absorption-promoting effect can be expected by using two or more of absorption-promoting agents as described above together.

Besides, the additive includes hydrocarbons, various surfactants, aliphatic alcohols such as myristyl alcohol, pentadecyl alcohol, cetyl alcohol, heptadecyl alcohol, stearyl alcohol and the like, straight-chain fatty acids such as pentadecanoic acid, palmitic acid, heptadecanoic acid, stearic acid, oleic acid and the like, and aliphatic esters such as methyl oleate, ethyl oleate, propyl oleate, methyl stearate, ethyl stearate, propyl stearate, butyl stearate, lauryl stearate, myristyl stearate, nonadecanoic acid methyl ester and the like, and the like.

A method for crosslinking includes a physical crosslinking treatment with radiation such as ultraviolet ray, electron beam, X ray, β ray, γ ray and the like, and a chemical crosslinking treatment which uses crosslinking agents such as polyisocyanate compound, organic peroxide, organometallic salt, metal alcoholate, metal-chelating compound, isocyanate compound, epoxy compound and the like. An amount of the crosslinking agent to be added in a layer of the pressure-sensitive adhesive is 0.001-10%, and preferably 0.05-1%.

An amount of a drug to be contained in the percutaneously absorbing preparation is properly set depending on a kind of a drug and an application site and is usually in a range of 1-60% by weight, preferably 2-40% by weight. When the content of a drug in the percutaneously absorbing preparation is below 1% by weight, release of a drug at an effective amount for treatment or prevention can not be expected. On the other hand, when the content of the drug exceeds 60% by weight, it is economically disadvantageous because enhancement of the effect can not be expected for increment of a drug. In addition, in the present invention, a whole drug contained in the percutaneously absorbing preparation is not necessarily dissolved in a layer of the pressure-sensitive adhesive, and a drug can be contained at an amount equal to or exceeding its solubility in a layer of the pressure-sensitive adhesive and dispersed in the undissolved state.

As the known percutaneously absorbing preparing techniques, there are those described in JP-A 9-77658, JP-A 9-12448, JP-A 9-176000, JP-A 9-301853, JP-A 9-169635, JP-A 10-130172, JP-A 10-179711, JP-A 10-298067, JP-A 10-306023, JP-A 11-92361, JP-A 11-104229, JP-A 11-292794 and the like, and the composition for promoting lacrimal secretion of the present invention may be prepared by utilizing these techniques.

Ophthalmic Preparation for Topical Administration

The composition for promoting lacrimal secretion of the present invention can be used as ophthalmic preparations for topical administration such as eyewash, eye drops, ophthalmic ointments, ophthalmic gels and the like.

In the case of an ophthalmic preparation for topical administration, an amount of the composition for promoting lacrimal secretion may be 0.00001-50% (w/v), preferably 0.0001-5% (w/v), and particularly 0.001-0.01% (w/v). When the amount is below 0.00001% (w/v), there is a possibility that the satisfactory lacrimal secretion promoting action is not perceived. On the other hand, when the amount exceeds 50% (w/v), there is a possibility that properties of a product itself such as the stability and the like is deteriorated. In the case of an aqueous eye drop, it is preferable that an osmotic pressure thereof is adjusted at 230-450 mOsm, and preferably 260-320 mOsm. In addition, it is suitable that a pH of an aqueous eye drop is adjusted to around 3.5-8.5, and preferably around 5.0-8.0.

It is said that an amount of lacrimal fluid on the surface of an eye is usually around 7 μL, and that a time during which an amount of a drug is decreased to a half level due to dilution or outflow by lacrimal fluid exchange on the surface of an eye is around 7 minutes. In the case of the aqueous eye drop, it is preferable that it is instilled one to several times per day, because a drug storage capacity of conjunctival sac is 10-30 μL, thereby, a large amount of the drug is not storable in the solution state.

In the case of ophthalmic topical administration, the dosage form of the composition for promoting lacrimal secretion includes solutions, ointments, ophthalmic inserting agents, gels, emulsions, suspensions and solid eye drops and the like, and may be properly selected therefrom. In addition, modifications such as sustained-releasing, stabilizing and easy-absorbing properties and the like may be further applied to such the preparations. These dosage forms are sterilized, for example, by filtration through a microorganism separating filter, heat sterilization or the like. In addition, a size of a particle contained in ophthalmic ointments or the like is preferably equal to or smaller than 75 µm.

The technique of drug delivery system (DDS) may be adopted for the dosage forms as described above. For example, a DDS preparation may be prepared in which the composition for promoting lacrimal secretion of the present invention is contained in an alginic acid matrix between membranes which are controlled releasing membranes of an insoluble ethylene-vinyl acetate copolymer. Such a DDS preparation can be continuously placed inside eyelids, and can continuously release a drug at a constant rate. A rate of releasing a drug is preferably 0.1 µg/h-10 mg/h, and more preferably 1 µg/h-100 µg/h.

In the case of an ophthalmic preparation for topical administration, a factor which influences on a contact time and a residence time of a drug becomes important. For this purpose, sustained release can be realized by adding a thickening agent to the ophthalmic preparation for topical administration, or formulating the ophthalmic preparation for topical administration into an oily or aqueous suspension, an oily solution or the like. For example, the ophthalmic preparation for topical administration can be formulated into a viscous eye drop or ophthalmic ointment with a gradually dissolving polymer (povidone and a water-soluble polymer) or the like added. In addition, sustained releasing property, absorbability and the like of a drug can be significantly enhanced by encapsulating the drug in ointments and liposomes.

The buffer to be used in the aqueous eye drop is particularly preferably a borate buffer. When the borate buffer is used as the buffer, a solution having a lower irritation as compared with the case where other buffers, for example, a phosphate buffer is used. Upon this, an amount of borate to be added is 0.01-10% (w/v), preferably 0.1-4% (w/v), and more preferably 0.5-2% (w/v).

In addition, additives such as solvents, bases, solution adjuvants, suspending agents, thickening agents, emulsifying agents, stabilizing agents, buffering agents, isotonicity adjusting agents, soothing agents, preservatives, corrigents, flavoring agents, coloring agents, excipients, binding agents, lubricants and the like can be added to a preparation, depending on the dosage forms (known dosage forms such as solutions, ointments, ophthalmic inserting agents, gels, emulsions, suspensions, solid eye drops and the like). Additionally, various additives such as pH adjusting agents, gelling agents, solubilizing agents, surfactants, sweetening agents, absorption-promoting agents, dispersing agents, preservatives, solubilizing agents and the like can be used.

Each of these additives is illustrated by way of embodiments below, but not limited thereto.

Solvents: distilled water, physiological saline solution, vegetable oils, liquid paraffin, mineral oils, propylene glycol, p-octyl dodecanol, ethanol, ethylene glycol, macrogol, glycerin, olive oil, sesame oil, peanut oil, caster oil, Isotonicity adjusting agents: sodium chloride, boric acid, sodium citrate, potassium chloride, borax, propylene glycol, glycerin, glucose, sorbitol, mannitol, trehalose, Buffering agents: boric acid, phosphoric acid, acetic acid, citric acid, carbonic acid, tartaric acid and salts thereof, borax, sodium citrate, sodium glutamate, sodium aspartate, Stabilizing agents: sodium sulfite, propylene glycol, Chelating agents: edetic acid and salts thereof, nitrilotriacetic acid and salts thereof, trihydroxymethylaminomethane, citric acid, sodium hexametaphosphate, Thickening agents: glycerin, carboxyvinyl polymer, chondroitin sulfate, polyvinyl alcohol, polyvinyl pyrrolidone, hydroxyethyl cellulose, hydroxypropyl cellulose, methyl cellulose, hydroxypropylmethyl cellulose, carboxymethyl cellulose and salts thereof, sodium alginate, macrogol 4000, gum arabic, gelatin, Bases: vaseline, purified lanolin, zeren 50, plastibase, macrogol, liquid paraffin, polyethylene glycol, carboxymethyl cellulose, Gelling agents: carboxymethyl cellulose, methyl cellulose, carboxyvinyl polymer, ethylene malic anhydride polymer, polyoxyethylene-polyoxypropylene block copolymer, gellan gum, Excipients: crystalline cellulose, Binding agents: hydroxypropyl cellulose, hydroxypropylmethyl cellulose, gelatin, polyvinyl pyrrolidone, Lubricants: magnesium stearate, hydrogenated caster oil, talc, Stabilizing agents: editates, sodium citrate, sodium hydrogensulfite, ethylenediaminetetraacetates, PH adjusting agents: hydrochloric acid, sodium hydroxide, phosphoric acid, citric acid, malic acid, tartaric acid, fumaric acid, lactic acid, succinic acid, ascorbic acid, acetic acid, Binding agents: hydroxypropyl cellulolse, hydroxypropylmethyl cellulose, gelatin, Suspending agents: methyl cellulose, sodium carboxymethyl cellulose, carboxyvinyl polymer, hydroxypropylmethyl cellulose, polyvinyl alcohol, polyvinyl pyrrolidone, polyethylene glycol, sodium chondroitin sulfate, polysorbate 80, Bactericides: benzethonium chloride, chlorhexidine gluconate, Antioxidants: sulfites, ascorbic acid, α-tocopherol, cysteine, Coloring agents: tar pigments, riboflavin, licorice extracts, zinc oxide, Wetting agents: terpenoids (menthol, borneol, camphor, geraniol, anethole, limonene, eugenol).

In addition to the above additives, drugs such as antibiotics, antivirals, anti-inflammatory drugs, antiallergics, vasoconstrictors, local anesthetics, analgesics, intraocular pressure-lowering agents, immunoregulators, vitamins and the like can be incorporated in the composition for promoting lacrimal secretion of the present invention, so long as they does not deteriorate the object of the present invention.

Such drugs are illustrated by way of embodiments below, but not limited thereto.

Antibiotics: aminoglucosides, quinolones, new quinolones, macrolides, cephems,

Sulfa drugs: sulfamethoxazole, sulfisoxazole, sulfisomidine, sulfadiazine, sulfadimethoxine, sulfamethoxypyridazine, Antivirals: famciclovir, penciclovir, aciclovir, Nonsteroidal anti-inflammatory drugs:

indomethacin, diclofenac, pranoprofen, tiaprofenic acid, tolfenamic acid

Steroidal anti-inflammatory drugs: prednisolone,

Anti-inflammatories: dipottasium glycyrrhizinate, allantoin, ε-aminocaprbic acid, berberine chloride, berberine sulfate, sodium azulenesulfonate, zinc sulfate, zinc lactate, lysozyme chloride, Antiallergics: ketotifen, oxatomide, cetirizine, sodium cromoglicate, Antihistamines: mequitazine, chlorpheniramine maleate, diphenhydramine hydrochloride, Vasoconstrictors: naphazoline, tetrahydrozoline, oxymethazoline, phenylephrine, ephedrines, epinephrine and the like, and salts thereof, Local anesthetics: lidocaine hydrochloride, procaine hydrochloride, dibucaine hydrochloride, Cholinolytics: belladonna alkaloid, flutropium bromide, tropicamide, Antiphlogistic enzymes: lysozyme chloride, serrapeptase, bromelain, Miotics: pilocarpine hydrochloride Galenical extracts: barren-worts, licorice, oriental bezoar, ginseng, coix seed, Japanese angelica root, bupleurum root, cinnamon bark, schisandra fruit, lithospermum root, Flavoring agents and refreshing agents: menthols, camphors, borneols, eucaliptus, geraniols, fennels, peppermints, Anti-cholinoesterases: neostigmine methylsulfate.

In addition, in the ophthalmic preparation for topical administration, the known vitamins, for example, vitamin A, vitamin C, vitamin E, vitamin $B_1$, $B_2$, $B_6$, $B_{12}$, and the like as well as derivatives thereof can be used alone or in combination of two or more thereof. Retinol as a derivative of vitamin A, ascorbates as derivatives of vitamin C, tocopherol succinate as a derivative of vitamin E, bisibutiamine as a derivative of vitamin $B_1$, flavin adenine dinucleotide as a derivative of vitamin $B_2$, salts of pyridoxine and pyridoxal as derivatives of vitamin $B_6$, hydroxocobalamin as a derivative of vitamin $B_{12}$, and the like can be used. In addition, other vitamins such as nicotinates, pantothenates, biotin and the like can be used.

In the eye drop, a preferable amount of vitamins to be added is, 0.1-10% (w/v), preferably 0.25-5% (w/v) of vitamin A and derivatives thereof, 0.01-0.5% (w/v), preferably 0.03-0.3% (w/v) of vitamin $B_1$ and derivatives thereof, 0.005-0.3% (w/v), preferably 0.01-0.2% (w/v) of vitamin $B_2$ and derivatives thereof, 0.01-0.5% (w/v), preferably 0.03-0.3% (w/v) of vitamin $B_6$ and derivatives thereof, 0.000005-0.003% (w/v), preferably 0.00001-0.0015% (w/v) of vitamin $B_{12}$ and derivatives thereof, 0.005-0.2% (w/v), preferably 0.01-0.1% (w/v) of vitamin C and derivatives thereof, and 0.005-0.2% (w/v), preferably 0.01-0.1% (w/v) of vitamin E and derivatives thereof. When nicotinic acid amide is used, the concentration thereof is preferably 0.01-1% (w/v), and more preferably 0.05-0.5% (w/v).

In addition, amino acids as an osmoregulating chemical, a nutrient source or the like, water-soluble polymers as an osmoregulating chemical, a thickening agent or the like, neutral salts as an osmoregulating chemical, lacrimal fluid ingredients equivalent or the like and the like can be added.

The amino acids include, for example, ε-aminocaproic acid, glutamic acid, lysine, histidine, leucine, methionine, phenylalanine and the like. In addition, upon incorporation of the amino acid in the aqueous eye drop composition of the present invention, the amino acids may be added as such or in the form of salts thereof. Such salts include, for example, sodium glutamate, lysine hydrochloride, histidine hydrochloride and the like. When the amino acid is used, the concentration thereof is preferably 0.01-1% (w/v), and more preferably 0.05-0.5% (w/v).

The water-soluble polymers include, for example, polyvinyl pyrrolidone, hydroxypropylmethyl cellulose, polyvinyl alcohol, carboxymethyl cellulose and the like. The concentration of the water-soluble polymer is preferably 0.1-5% (w/v), and more preferably 0.3-3% (w/v).

The neutral salts include, for example, sodium chloride, calcium chloride, magnesium chloride, sodium sulfate, calcium sulfate, magnesium sulfate, sodium nitrate, calcium nitrate and magnesium nitrate, and particularly preferred among them are sodium chloride, calcium chloride, magnesium chloride and magnesium sulfate. Preferably, the concentration of the neutral salts should be determined considering the osmotic pressure.

The solution adjuvants may be used in the ophthalmic preparation for topical administration of the present invention. The solution adjuvants include, for example, cyclodextrin, polyvinyl pyrrolidone, caffeine, propylene glycol, benzyl benzoate, ethanol, trisaminomethane, mannitol, sodium carbonate, sodium citrate, taurine, nonionic surfactants such as polyoxyethylenesorbitan mono higher fatty acid ester (polyoxypolyoxyethylenesorbitan monooleate, polyoxyethyleneoxystearic acid triglyceride and the like), polyethylene glycol, polyoxyethylene hydrogenated castor oil, polyoxyethylenesorbitan monooleate, polyoxyethylene monostearyl, polyoxyethylene lauryl ether, monolaurate decaglyceryl, polyoxyethylene polyoxypropylene glycol and the like. The nonionic surfactants to be used in the eye drop and the like are known to have the relatively low irritation for mucosa and cornea and, therefore, they are widely used. The concentration of the nonionic surfactant is preferably 0.01-10% (w/v), more preferably 0.05-5% (w/v), and yet more preferably 0.1-2% (w/v). Other surfactants include anionic surfactants (alkyl sulfate, sodium lauryl sulfate, sodium lauroyl sarcosinate), but it is not preferable that they are used in the eye drop because they have irritation for mucosa and the like, although they have the strong dissolution aiding action.

In addition, a preservative and an antiseptic are preferably contained in the ophthalmic preparation for topical administration. The preservative includes, for example, phenolic substances such as phenol, cresol and paraoxybenzoic acid esters, alcohols such as chlorobutanol, propylene glycol and the like, acidic substances such as benzoic acid, dehydroacetic acid and the like and salts thereof, quaternary ammonium salts such as benzalkonium chloride, benzethonium chloride and the like, polyethyleneoxide-containing high molecular quaternary ammonium compounds, thimerosal and the like.

The antiseptic is preferably prepared in the concentration between 0.0001% (w/v) and 5% (w/v), and includes quaternary ammonium salts such as benzalkonium chloride, benzethonium chloride, cetylpyridinium chloride and the like, paraoxybenzoic acid esters such as methyl paraoxybenzoate, ethyl paraoxybenzoate, propyl paraoxybenzoate, butyl paraoxybenzoate and the like, benzyl alcohol, phenethyl alcohol, chlorobutanol, thiomersal, thimerosal, methylparaben, propylparaben, disodium editate, sorbic acid and salts thereof, sodium dehydroacetate and the like.

In addition, as described above, sustained effects can be expected by using together an aminopeptidase inhibitor because it is known that many peptides which activate PAR are degraded by aminopeptidase in a living body. Amastatine, Arphamenine A, Arphamenine B, bestatin and the like are known as the aminopeptidase inhibitor, and these compounds may be contained in or may be used together with the preparation. Also, in the case where the component as described above is not a peptide, the substance which inactivates or degrades the component may be contained in or may be used together with the preparation to sustain the effects of the component.

For dry eye derived from abnormal lipid secretion due to meibomian glands dysfunction, a trace amount of oils such as caster oil, liquid paraffin and the like may be added in the preparation, in addition to the composition for promoting lacrimal secretion of the present invention.

Ingredients which are used in the conventional composition other than above ingredients can be used in the preparation, and an amount of these ingredients to be added may be a usual amount so long as they do not deteriorate the effects of the present invention.

When an insoluble drug or the like is contained in the composition for promoting lacrimal secretion of the present invention, known techniques such as those described in JP-A 11-29463 may be used to obtain a stable aqueous suspension.

Preparation for Contact Lens

The composition for promoting lacrimal secretion of the present invention can be applied to an eye drop for contact lens, a washing solution for contact lens and a preserving solution for contact lens, and a contact lens composition.

When the composition of the present invention is used as eye drops for contact lens, washing solution for contact lens and preserving solution for contact lens, it is preferable that a surfactant be incorporated therein. The effect of preventing adsorption of a phospholipid-like polymer to the contact lens can be effected by incorporating the surfactant therein.

The surfactant includes nonionic surfactants such as polyoxyethylene-polyoxypropylene block copolymer, polyoxyethylene/polyoxypropylene-substituted ethylenediamine, Polysorbate 80, polyoxyethylene hydrogenated castor oil, polyoxyethylenestearate and the like, amphoteric surfactants such as alkylpolyaminoethyl glycine and the like, and anionic surfactants such as alkylbenzene sulfonate, alkyl sulfate and the like and, among them, nonionic surfactants are the most preferable in light of safety to eyes. An amount of the surfactant to be incorporated is preferably 0.001-5%, and more preferably 0.01-1%.

The eye drop for contact lens, the washing solution for contact lens and the preserving solution for contact lens having a generally used composition may be used, and the additives to be used therein may be properly selected from the additives described above for the ophthalmic preparation for topical administration. The eye drop for contact lens, the washing solution for contact lens and the preserving solution for contact lens may be produced according to the method similar to that as described above for the ophthalmic preparation for topical administration.

In addition, a drug-sustained releasing contact lens may be produced in which the composition for promoting lacrimal secretion of the present invention is retained in and/or adhered to a contact lens.

The contact lens may be produced using the known materials. For example materials for water-containing soft ophthalmic lens as described in JP-A 9-80358, 2-hydroxyethyl methacrylate polymers as described in JP-A 9-124715, ophthalmic lens materials as described in JP-A 9-189887, molded ophthalmic collagen gels as described in JP-A 11-197234, the hydrogel lens which is coated with a lipid layer in advance as described in JP-A 9-101488 and the like may be used. Additionally, known materials such as methacrylic acid ester polymers, copolymers of oligosiloxanylalkyl(meth)acrylate monomers/methacrylic acid ester monomer and the like may be used.

Generally used contact lens such as hard or rigid cornea-type lens, and gel, hydrogel or soft-type lens which are produced from the above known materials may be used.

The drug sustained-releasing contact lens may be produced, for example, by incorporating in or adhering to the contact lens the composition for promoting lacrimal fluid secretion of the present invention according to the known methods for producing the drug sustained-releasing contact lens as described in JP-A 8-24325, JP-A 11-24010, JP-A 10-339857 and the like.

Specifically, the drug sustained-releasing contact lens may be produced by adhering to a part of the contact lens a finely-divided or gel drug sustained-releasing agent which is prepared from a component which activate PAR-2 and polymers such as polyvinyl pyrrolidone, sodium hyaluronate and the like. In addition, the drug sustained-releasing contact lens may be produced by forming a drug reservoir such as by producing a contact lens from a member which forms a front surface of the lens and a member which forms a rear surface of the lens. Also, the contact lens of the present invention may be produced according to the known methods for producing the drug sustained-releasing contact lens other than those described above.

The present invention will be further illustrated below by way of Examples, but the present invention is not limited thereto.

EXAMPLE 1

Method for Synthesizing Various Peptides

Various peptides, components of the present invention which activate PAR-2, were synthesized according to the known method (Carpino, L. A. et al., J. Org. Chem., 37, 3404-3409, 1972). Method for synthesizing Ser-Leu-Ile-Gly-Arg-Leu-NH$_2$ (SEQ ID NO:1, SLp-NH$_2$)

1.33 g (0.17 meq/g) of Fmoc-PAL-PEG-PS-resin (PE Biosystems) was weighed, and 10 mL of dimethylformamide was added thereto to stand for 2-3 hours, and the resin was swelled and filled in a column for peptide synthesis.

The column for peptide synthesis was prepared according to the above method, and 283 mg of Fmoc-L-Leu-OH (WAKO), 519 mg of Fmoc-L-Arg(Pbf)-OH (PE Biocystems), 238 mg of Fmoc-L-Gly-OH (BACHEM), 283 mg of Fmoc-L-Ile-OH (WAKO), 283 mg of Fmoc-L-Leu-OH (WAKO) or 307 mg of Fmoc-L-Ser(tBu)-OH (PE Biosystems) was separately weighed in a tube, and 380 mg of HATU (O-(7-azabenzotriazole-1-yl)-1,1,3,3-tetramethyluronium hexafluorophosphate) (PE Biosystems) was added to each tube. Amino acids described above were placed in an order from the C-terminal, and synthesis was performed using a peptide synthesizer PIONEER (PE Biosystems). The synthesized peptide-resin was treated with a mixture of TFA-H$_2$O-phenol-triisopropylsilane (8.8:0.5:0.5:0.2) for 3 hours, the resin was filtered, then the filtrate was recrystallized from an ether to obtain a crude peptide. Then, the crude peptide was purified by subjecting to HPLC (A: 0.02% TFA in water, B: 0.02% TFA in 50% CH$_3$CN). The fraction containing purified peptide was lyophilized to obtain Ser-Leu-Ile-Gly-Arg-Leu-NH$_2$ (SEQ ID NO:1).

Method for Synthesizing Ser-Leu-Ile-Gly-Arg-Leu-OH (SEQ ID NO:2, SLp-OH)

1.00 g (0.21 meq/g) of Fmoc-L-Leu-PEG-PS-resin (PE Biosystems) was weighed, and 10 mL of dimethylformamide was added thereto to stand for 2-3 hours, and the resin was swelled and filled in a column for peptide synthesis.

519 mg of Fmoc-L-Arg(Pbf)-OH (PE Biosystems), 238 mg of Fmoc-L-Gly-OH (BACHEM), 283 mg of Fmoc-L-Ile-OH (WAKO), 283 mg of Fmoc-L-Leu-OH (WAKO) or 307 mg of Fmoc-L-Ser(tBu)-OH (PE Biosystem) was separately weighed in a tube, and 380 mg of HATU was added thereto. Amino acids described above were placed in an order from the C-terminal, and synthesis was performed using a peptide synthesizer PIONEER. The crude peptide was obtained from the synthesized peptide-resin and, thereafter, it was purified by subjecting to HPLC. The fraction containing purified peptide was lyophilized to obtain Ser-Leu-Ile-Gly-Arg-Leu-OH (SEQ ID NO:2).

Method for Synthesizing Trans-Cynnamoyl-Leu-Ile-Gly-Arg-Leu-Ornithine-$NH_2$ (SEQ ID NO:3)

This peptide was synthesized according to the known method (Carpino, L. A. et al., J. Org. Chem., 37, 3404-3409, 1972).

Method for Synthesizing Ser-Phe-Leu-Leu-Arg-$NH_2$ (SEQ ID NO:4)

1.33 g (0.17 meq/g) of Fmoc-PAL-PEG-PS-resin (PE Biosystems) was weighed, and 10 mL of dimethylformamide was added thereto to stand for 2-3 hours, and the resin was swelled and filled in a column for peptide synthesis.

519 mg of Fmoc-L-Arg(Pbf)-OH (PE Biosystems), 283 mg of Fmoc-L-Leu-OH (WAKO), 283 mg of Fmoc-L-Leu-OH (WAKO), 305 mg of Fmoc-L-Phe-OH (WAKO) or 307 mg of Fmoc-L-Ser(tBu)-OH (PE Biosystems) was separately weighed in tube, and 380 mg of HATU (PE Biosystems) was added thereto. Amino acids described above were placed in an order from the C-terminal, and synthesis was performed using a peptide synthesizer PIONEER (PE Biosystems). The synthesized peptide-resin was treated with a mixture of TFA-$H_2$O-phenol-triisopropylsilane (8.8:0.5:0.5:0.2) for 3 hours, filtered, then the filtrate was recrystallized from an ether to obtain a crude peptide. Then, the crude peptide was purified by subjecting to HPLC (A: 0.02% TFA in water, B: 0.02% TFA in 50% $CH_3CN$). The fraction containing purified peptide was lyophilized to obtain Ser-Phe-Leu-Leu-Arg-$NH_2$ (SEQ ID NO:4).

Method for Synthesizing Leu-Arg-Gly-Ile-Leu-Ser-$NH_2$ (SEQ ID NO:5, LRp-$NH_2$)

A column for peptide synthesis was prepared according to the above method, and 307 mg of Fmoc-L-Ser(tBu)-OH (PE Biosystems), 283 mg of Fmoc-L-Leu-OH (WAKO), 283 mg of Fmoc-L-Ile-OH (WAKO), 238 mg of Fmoc-L-Gly-OH (BACHEM), 519 mg of Fmoc-L-Arg(Pbf)-OH (PE Biosystems), or 283 mg of Fmoc-L-Lew-OH (WAKO) was separately weighed in a tube, and 380 mg of HATU was added thereto. Amino acids described above were placed in an order from the C-terminal, and synthesis was performed using a peptide synthesizer PIONEER. The crude peptide was obtained from the synthesized peptide-resin according to the method described above, and purified by subjecting to HPLC. The fraction containing purified peptide was lyophilized to obtain Leu-Arg-Gly-Ile-Leu-Ser-$NH_2$ (SEQ ID NO:5).

EXAMPLE 2

An Animal which was Used in Experiments

Male Wistar-line rat at 6 weeks of age was used in experiments. Each animal was housed for one week under the environment of room temperature of 23±2° C., a humidity of 50±5% and a 12 hours light/dark cycle (light: 07:00-19:00) and, thereafter, it was subjected to experiments. During the housing and experiment period, the animal was fed a solid chow and water ad lib.

Four animals were used in Examples 3-4, and the results thereof are shown in the mean±S.E.M. The test of significance was performed according to a Tukey's multiple comparison test.

EXAMPLE 3

The effect of PAR-2 agonist peptide on a rat lacrimal secretion in vivo was investigated (FIG. 1).

An amount of rat lacrimal fluid was measured according to the method of Iga et al. (Iga, Y. et al., Jpn. J. Pharmacol., 78, 373-80, 1998). That is, the rat was anesthetized with pentobarbital (50 mg/kg, intraabdominal administration), and a paper with 2 mm width for testing human lacrimal secretion function, the Schirmer test paper (Showa Yakuhin Kako Co., Ltd.) was inserted into a lower eyelid of the rat. After the period of time fixed has passed, the test paper was removed, and a length of a wetted portion of the test paper was measured using a caliper square. An amount of lacrimal fluid was measured at 1, 2, 4, 6, 8 and 10 minutes after intravenous administration of a solvent or PAR-associated peptides.

When 5 μmol/kg of a PAR-2 agonist peptide, SLp-$NH_2$ was administered to the rat intravenously, significant promotion of lacrimal secretion was observed with a peak 1 minute after the intravenous administration. Then, the effect of SLp-$NH_2$, in combination with amastatine, which is an aminopeptidase inhibitor, on the lacrimal secretion promoting action of SLp-$NH_2$ was investigated, in light of that many PAR-2 agonist peptides are known to be degraded by aminopeptidase (Godin, D. et al., Eur. J. Pharmacol., 253, 225-30, 1994). Amastatine (Peptide Lab.) was intravenously administered at 2.5 μmol/kg 1 minute before administration of SLp-$NH_2$. As the result, a significant promotion of lacrimal secretion having a peak 1 minute after the administration was observed in SLp-$NH_2$ alone. In the combined treatment, however, the action thereof was more persistent than that of SLp-$NH_2$ alone, and a significant promotion of lacrimal secretion was observed 8 and 10 minutes after the treatment as compared with SLp-$NH_2$ alone.

EXAMPLE 4

Figure 2:
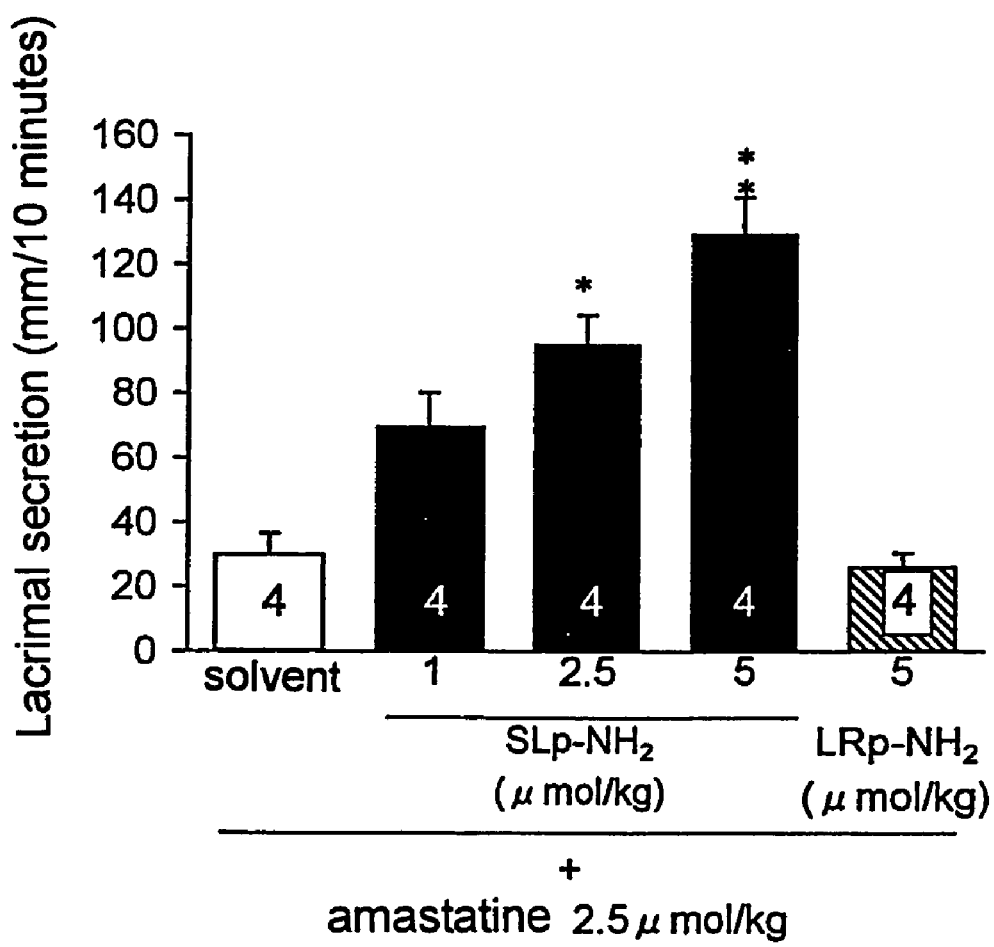
FIG. 2 is a graph illustrating a dose-dependency of the rat lacrimal secretion promoting activity by PAR-2 agonist peptide for vivo. *<0.05, **<0.01 vs solvent (Tukey test).

Dose-dependency in the promoting action of rat lacrimal secretion by the PAR-2 agonist peptide in vivo was investigated (FIG. 2).

An amount of lacrimal fluid was measured as described in Example 3.

The SLp-$NH_2$ promoted the rat lacrimal secretion in doses of ranging from 1 to 5 μmol/kg in a dose-dependent manner. On the other hand, a control peptide, LRp-$NH_2$ had no effect on the rat lacrimal secretion even at 5 μmol/kg, and resulted in an amount of lacrimal secretion similar to that of a solvent-administrated group.

The formulations of the compositions of the present invention manufactured according to the conventional method are shown in each table in the following Examples.

EXAMPLE 5

Tablet

TABLE 1

| | |
|---|---|
| Crystalline cellulose | 18 mg |
| SLp-$NH_2$ | 15 mg |
| Low-substituted hydroxypropyl cellulose | 12 mg |
| Hydroxypropylmethyl cellulose | 10 mg |

TABLE 1-continued

| | |
|---|---|
| Magnesium stearate | 1 mg |
| Lactose | q.s. |
| Total | 100 mg |

EXAMPLE 6

Tablet

TABLE 2

| | |
|---|---|
| Amastatine | 20 mg |
| Crystalline cellulose | 18 mg |
| SLp-NH$_2$ | 15 mg |
| Low-substituted hydroxypropyl cellulose | 12 mg |
| Hydroxypropylmethyl cellulose | 10 mg |
| Magnesium stearate | 1 mg |
| Lactose | q.s. |
| Total | 100 mg |

EXAMPLE 7

Capsule

TABLE 3

| | |
|---|---|
| SLp-NH$_2$ | 15 mg |
| Low-substituted hydroxypropyl cellulose | 15 mg |
| Cross-linked sodium carboxymethyl cellulose | 5 mg |
| Magnesium stearate | 2 mg |
| Lactose | 63 mg |
| Total | 100 mg |

EXAMPLE 8

Capsule

TABLE 4

| | |
|---|---|
| SLp-NH$_2$ | 15 mg |
| Low-substituted hydroxypropyl cellulose | 15 mg |
| Amastatine | 5 mg |
| Cross-linked sodium carboxymethyl cellulose | 5 mg |
| Magnesium stearate | 2 mg |
| Lactose | 63 mg |
| Total | 100 mg |

EXAMPLE 9

Injection

TABLE 5

| | |
|---|---|
| Dextrose | 10 mg |
| SLp-NH$_2$ | 1 mg |
| Amastatine | 1 mg |
| Purified water for injection | q.s. |
| Total | 200 mL |

EXAMPLE 10

Eye Drop (Aqueous Eye Drop)

TABLE 6

| | |
|---|---|
| SLp-NH$_2$ | 10 mg |
| Sodium chloride | 90 mg |
| Hydrochloric acid | q.s. |
| Sodium hydroxide | q.s. |
| Sterilized purified water | q.s. |
| Total | 100 mL |

EXAMPLE 11

Eye Drop (Aqueous Eye Drop)

TABLE 7

| | |
|---|---|
| SLp-NH$_2$ | 50 mg |
| Boric acid | 1700 mg |
| Methyl paraoxybenzoate | 28 mg |
| Propyl paraoxybenzoate | 12 mg |
| Sodium editate | 5 mg |
| Borax | q.s. |
| Sterilized purified water | q.s. |
| Total | 100 mL |

EXAMPLE 12

Eye Drop (Aqueous Eye Drop)

TABLE 8

| | |
|---|---|
| SLp-NH$_2$ | 1 mg |
| Boric acid | 700 mg |
| Borax | q.s. |
| Sodium chloride | 510 mg |
| Sodium editate | 0.06 mg |
| Benzalkonium chloride | 0.005 mg |
| Sterilized purified water | q.s. |
| Total | 100 mL |

EXAMPLE 13

Eye Drop (Aqueous Eye Drop)

TABLE 9

| | |
|---|---|
| SLp-NH$_2$ | 200 mg |
| Allantoin | 100 mg |
| Chlorpheniramine maleate | 30 mg |
| Boric acid | 1700 mg |
| Sodium citrate | 220 mg |
| Chlorhexidine gluconate | 5 mg |
| Borax or hydrochloric acid | q.s. |
| Sterilized purified water | q.s. |
| Total | 100 mL |

EXAMPLE 14

Eye Drop (Aqueous Eye Drop)

TABLE 10

| | |
|---|---|
| SLp-NH$_2$ | 1000 mg |
| Pyridoxine hydrochloride | 100 mg |
| Aminoethylsulfonic acid | 1000 mg |
| Chlorpheniramine maleate | 50 mg |
| Boric acid | 1000 mg |
| Sodium citrate | 220 mg |
| Chlorhexidine gluconate | 2.5 mg |
| Sodium hydroxide or hydrochloric acid | q.s. |
| Sterilized purified water | q.s. |
| Total | 100 mL |

EXAMPLE 15

Eye Drop (Aqueous Eye Drop)

TABLE 11

| | |
|---|---|
| SLp-NH$_2$ | 500 mg |
| Cyanocobalamin | 20 mg |
| Potassium L-aspartic acid | 1000 mg |
| Concentrated glycerol | 1400 mg |
| Sodium citrate | 200 mg |
| Chlorhexidine gluconate | 5 mg |
| Sodium hydroxide or hydrochloric acid | q.s. |
| Distilled purified water | q.s. |
| Total | 100 mL |

EXAMPLE 16

Eye Drop (Aqueous Eye Drop)

TABLE 12

| | |
|---|---|
| SLp-NH$_2$ | 2000 mg |
| Flavin adenine dinucleotide | 50 mg |
| Cyanocobalamin | 20 mg |
| Sodium chloride | 900 mg |
| Sodium citrate | 200 mg |
| Chlorhexidine gluconate | 2.5 mg |
| Sodium hydroxide or hydrochloric acid | q.s. |
| Sterilized purified water | q.s. |
| Total | 100 mL |

EXAMPLE 17

Eye Drop (Aqueous Eye Drop)

TABLE 13

| | |
|---|---|
| SLp-NH$_2$ | 250 mg |
| Sodium acetate | 100 mg |
| Concentrated glycerin | 2600 mg |
| Methyl paraoxybenzoate | 20 mg |
| Propyl paraoxybenzoate | 10 mg |
| Chlorobutanol | 250 mg |
| Polyvinyl pyrrolidone | 1000 mg |
| Sterilized purified water | q.s. |
| Total | 100 mL |

EXAMPLE 18

Eye Drop (Aqueous Eye Drop)

TABLE 14

| | |
|---|---|
| SLp-NH$_2$ | 25 mg |
| Concentrated glycerin | 2600 mg |
| Polysorbate 80 | 100 mg |
| Benzalkonium chloride | 5 mg |
| Sterilized purified water | q.s. |
| Total | 100 mL |

EXAMPLE 19

Eye Drop (Aqueous Eye Drop)

TABLE 15

| | |
|---|---|
| SLp-NH$_2$ | 500 mg |
| Boric acid | 800 mg |
| Borax | 200 mg |
| Sodium hydroxide | 500 mg |
| Chlorobutanol | 300 mg |
| Sterilized purified water | q.s. |
| Total | 100 mL |

EXAMPLE 20

Eye Drop (Aqueous Eye Drop)

TABLE 16

| | |
|---|---|
| SLp-NH$_2$ | 0.1 mg |
| Sodium lauryl sulfate | 600 mg |
| Polyoxyethylene lauryl ether (BL-25) | 3000 mg |
| Boric acid | 1700 mg |
| Benzalkonium chloride | 10 mg |
| Sodium hydroxide | q.s. |
| Sterilized purified water | q.s. |
| Total | 100 mL |

EXAMPLE 21

Eye Drop (Aqueous Eye Drop)

TABLE 17

| | |
|---|---|
| SLp-NH$_2$ | 150 mg |
| Sodium acetate | 50 mg |
| Benzalkonium chloride | 5 mg |
| Sodium chloride | 650 mg |
| Human serum albumin | 100 mg |
| Sodium hydroxide | q.s. |
| Diluted hydrochloric acid | q.s. |
| Sterilized purified water | q.s. |
| Total | 100 mL |

EXAMPLE 22

Eye Drop (Aqueous Eye Drop)

TABLE 18

| | |
|---|---|
| SLp-NH$_2$ | 700 mg |
| Boric acid | 2000 mg |
| α-cyclodextrin | 5000 mg |
| Borax | q.s. |
| Benzalkonium chloride | 5 mg |
| Sterilized purified water | q.s. |
| Total | 100 mL |

EXAMPLE 23

Eye Drop (Aqueous Eye Drop)

TABLE 19

| | |
|---|---|
| SLp-NH$_2$ | 5000 mg |
| Boric acid | 1600 mg |
| Borax | 1000 mg |
| Polyvinyl pyrrolidone K30 | 2000 mg |
| Caffeine | 2000 mg |
| Polyethylene glycol (average molecular weight 4000) | 5000 mg |
| Methyl paraoxybenzoate | 260 mg |
| Propyl paraoxybenzoate | 140 mg |
| Hydrochloric acid | q.s. |
| Sterilized purified water | q.s. |
| Total | 1000 mL |

EXAMPLE 24

Eye Drop (Aqueous Eye Drop)

TABLE 20

| | |
|---|---|
| SLp-NH$_2$ | 25 mg |
| Vitamin B2 | 50 mg |
| Vitamin B6 | 100 mg |
| Vitamin B12 | 0.5 mg |
| Naphazoline hydrochloride | 50 mg |
| Flutropium bromide | 20 mg |
| Sterilized purified water | q.s. |
| Total | 100 mL |

EXAMPLE 25

Eye Drop (Aqueous Eye Drop)

TABLE 21

| | |
|---|---|
| SLp-NH$_2$ | 10 mg |
| Vitamin B$_2$ | 50 mg |

TABLE 21-continued

| | |
|---|---|
| Vitamin B$_6$ | 100 mg |
| Vitamin E | 30 mg |
| Oxymethazoline hydrochloride | 25 mg |
| Fluticasone propionate | 50 mg |
| Lysozyme chloride | 250 mg |
| Lidocaine hydrochloride | 300 mg |
| 1-menthol | 10 mg |
| Sterilized purified water | q.s. |
| Total | 100 mL |

EXAMPLE 26

Eye Drop (Aqueous Eye Drop)

TABLE 22

| | |
|---|---|
| SLp-NH$_2$ | 1 mg |
| Allantoin | 5 mg |
| Neostigmine methylsulfate | 5 mg |
| Flavin adenine dinucleotide | 10 mg |
| ε-aminocapron | 100 mg |
| Boric acid | 2000 mg |
| Sodium hydroxide | q.s. |
| Sterilized purified water | q.s. |
| Total | 100 mL |

EXAMPLE 27

Eye Drop (Aqueous Suspended Eye Drop)

TABLE 23

| | |
|---|---|
| SLp-NH$_2$ | 1000 mg |
| Sodium acetate | 100 mg |
| Sodium chloride | 900 mg |
| Hydroxypropylmethyl cellulose | 200 mg |
| Methyl paraoxybenzoate | 20 mg |
| Propyl paraoxybenzoate | 10 mg |
| 0.1 N hydrochloric acid | q.s. |
| Sterilized purified water | q.s. |
| Total | 100 mL |

EXAMPLE 28

Eye Drop (Aqueous Eye Drop of Dissolving Before Use-Type)
[Lyophilized Preparation]

TABLE 24

| | |
|---|---|
| SLp-NH$_2$ | 100 mg |
| Human serum albumin | 1 g |
| Sterilized purified water | q.s. |
| Total | 100 mL |

[Dissolving Solution]

TABLE 25

| | |
|---|---|
| Sodium acetate | 50 mg |
| Benzalkonium chloride | 5 mg |
| Sodium chloride | 650 mg |
| Sodium hydroxide | q.s. |
| Diluted hydrochloric acid | q.s. |
| Sterilized purified water | q.s. |
| Total | 100 mL |

EXAMPLE 29

Eye Drop (Oily Eye Drop)

TABLE 26

| | |
|---|---|
| SLp-NH$_2$ | 1 mg |
| Cottonseed oil | q.s. |
| Total | 10 mL |

EXAMPLE 30

Eye Drop (Eye Drop for Contact Lens)

TABLE 27

| | |
|---|---|
| SLp-NH$_2$ | 10 mg |
| Poloxamer 407 | 100 mg |
| Sodium chloride | 500 mg |
| Boric acid | 700 mg |
| Borax | 50 mg |
| Potassium sorbate | 200 mg |
| Sterilized purified water | q.s. |
| Total | 100 mL |

EXAMPLE 31

Eye Drop (Eye Drop for Contact Lens)

TABLE 28

| | |
|---|---|
| SLp-NH$_2$ | 500 mg |
| Polysorbate 80 | 100 mg |
| Sodium chloride | 500 mg |
| Potassium chloride | 150 mg |
| Sodium dihydrogenphosphate | 200 mg |
| Borax | 300 mg |
| Sterilized purified water | q.s. |
| Total | 100 mL |

EXAMPLE 32

Eye Drop (Eye Drop for Contact Lens)

TABLE 29

| | |
|---|---|
| SLp-NH$_2$ | 1 mg |
| Polysorbate 80 | 100 mg |
| Sodium chloride | 500 mg |
| Boric acid | 750 mg |
| Borax | 50 mg |
| Sterilized purified water | q.s. |
| Total | 100 mL |

EXAMPLE 33

Eye Drop (Eye Drop for Contact Lens)

TABLE 30

| | |
|---|---|
| SLp-NH$_2$ | 100 mg |
| Poloxamer 407 | 100 mg |
| Sodium chloride | 450 mg |
| Potassium chloride | 100 mg |
| Sodium dihydrogenphosphate | 200 mg |
| Borax | 200 mg |
| Alkylpolyaminoethyl glycine | 10 mg |
| Sterilized purified water | q.s. |
| Total | 100 mL |

EXAMPLE 34

Ophthalmic Ointment

TABLE 31

| | |
|---|---|
| SLp-NH$_2$ | 1 g |
| Glycerin | 2 g |
| Propylene glycol | 1 g |
| Liquid paraffin | 2 g |
| Ethyl paraoxybenzoate | 0.01 g |
| Propyl paraoxybenzoate | 0.01 g |
| Plastibase | q.s. |
| Total | 100 g |

EXAMPLE 35

Ophthalmic Ointment

TABLE 32

| | |
|---|---|
| SLp-NH$_2$ | 0.1 g |
| Liquid paraffin | 5 g |
| Ophthalmic white vaseline | q.s. |
| Total | 100.0 g |

EXAMPLE 36

Ophthalmic Ointment

TABLE 33

| | |
|---|---|
| SLp-NH$_2$ | 5 g |
| Liquid paraffin | 10 g |
| White vaseline | 80 g |

EXAMPLE 37

Ophthalmic Ointment

TABLE 34

| | |
|---|---|
| SLp-NH$_2$ | 0.01 g |
| Glycerin | 2 g |
| Propylene glycol | 1 g |
| Liquid paraffin | 2 g |
| Methyl paraoxybenzoate | 0.03 g |
| Propyl paraoxybenzoate | 0.01 g |
| White vaseline | q.s. |
| Total | 100 g |

EXAMPLE 38

Intraocularly Perfusing Washing Solution

TABLE 35

| | |
|---|---|
| SLp-NH$_2$ | 100 mg |
| Sodium chloride | 500 mg |
| Potassium chloride | 300 mg |
| Potassium chloride (anhydrous) | 100 mg |
| Magnesium sulfate (anhydrous) | 100 mg |
| Sodium acetate (trihydrate) | 600 mg |
| Sodium citrate (anhydrous) | 900 mg |
| Sodium hydrogen carbonate (anhydrous) | 200 mg |
| D-glucose (anhydrous) | 150 mg |

TABLE 33-continued

| | |
|---|---|
| Purified lanolin | 5 g |
| Total | 100.0 g |

TABLE 35-continued

| | |
|---|---|
| 1N hydrochloric acid | q.s. |
| Sterilized purified water | q.s. |
| Total | 100 mL |

INDUSTRIAL APPLICABILITY

As stated above, a composition for promoting lacrimal secretion of the present invention possesses the excellent lacrimal secretion promoting action and, thus, is the excellent therapeutic drug for dry eye resulted from the side effect of a drug, diseases, lowered function of lacrimal secretion or the like. In addition, the composition of the present invention can treat or prevent xerophthalmia, corneal afflux, foreign body feeling, itching feeling, paropsia, asthenopia, unpleasantness, burning feeling and the like followed by dry eye.

In addition, the composition for promoting lacrimal secretion of the present invention can be applied to an eye drop for contact lens, a washing solution for contact lens and a preserving solution for contact lens as well as a composition of contact lens.

SEQUENCE LISTING FREETEXT

SEQ ID NO:1
Designed peptide having PAR-2 agonist activity. The C-terminal amino acid residue is amidated.
SEQ ID NO:2
Designed peptide having PAR-2 agonist activity. The C-terminal amino acid residue is hydroxylated.
SEQ ID NO:3
Designed peptide having PAR-2 agonist activity. Xaa at 1 is trans-cynnamoyl-Leu. Xaa at 6 is Orn. The C-terminal amino acid residue is amidated.
SEQ ID NO:4
Designed peptide having PAR-1 and PAR-2 agonist activity. The C-terminal amino acid residue is amidated.
SEQ ID NO:5
Designed control peptide. The C-terminal amino acid residue is amidated.

What is claimed is:

1. A method for promoting lacrimal secretion comprising administering to a subject in need thereof, an effective amount of a peptide comprising a sequence selected from the group consisting of Ser-Leu-Ile-Gly-Arg-Leu-NH2 (SEQ ID NO:1), Ser-Leu-Ile-Gly-Arg-Leu-OH (SEQ ID NO:2), and trans-cynnamoyl-Leu-Ile-Gly-Arg-Leu-omithine-NH2 (SEQ ID NO: 3), together with a substance which inhibits inactivation or degradation of the peptide.

2. The method for promoting lacrimal secretion according to claim 1, wherein the substance is peptidase inhibitor.

3. The method for promoting lacrimal secretion according to claim 2, wherein said peptidase inhibitor is amastatine.

4. The method for promoting lacrimal secretion according to claim 1, wherein the peptide is formulated into an ophthalmic composition, wherein the ophthalmic composition has a form of an eye drop solution for contact lens, a preserving solution for the contact lens or a washing solution for contact lens.

* * * * *

UNITED STATES PATENT AND TRADEMARK OFFICE
CERTIFICATE OF CORRECTION

PATENT NO. : 7,348,306 B2
APPLICATION NO. : 11/211600
DATED : March 25, 2008
INVENTOR(S) : Hiromasa Araki It is certified that error appears in the above-identified patent and that said Letters Patent is hereby corrected as shown below:

Title Page
At Item (75) Inventors, line 1, delete "Yamatokaoriyama-shi" and insert
-- Yamatokoriyama-shi --.
At line 3, delete "Yamatokaoriyama-shi" and insert -- Yamatotakada-shi --.
On line 5, delete "Hiroyuki Nishikawa" and insert -- Sachiyo Nishimura --.
On line 6, delete "Sachiyo Nishimura" and insert -- Hiroyuki Nishikawa --.

Signed and Sealed this

Thirty-first Day of August, 2010

David J. Kappos
*Director of the United States Patent and Trademark Office*

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<221> NAME/KEY: AMIDATION
<222> LOCATION: 6
<223> OTHER INFORMATION: Designed peptide having PAR-2 agonist activity.
      The C-terminal amino acid residue is amidated.

<400> SEQUENCE: 1

Ser Leu Ile Gly Arg Leu
1               5

<210> SEQ ID NO 2
```

```
<211> LENGTH: 6
<212> TYPE: PRT
<213> ORGANISM: Artificial Sequence
<220> FEATURE:
<221> NAME/KEY: MOD_RES
<222> LOCATION: 6
<223> OTHER INFORMATION: Designed peptide having PAR-2 agonist activity.
      The C-terminal amino acid residue is hydroxylated.

<400> SEQUENCE: 2

Ser Leu Ile Gly Arg Leu
1               5

<210> SEQ ID NO 3
<211> LENGTH: 6
<212> TYPE: PRT
<213> ORGANISM: Artificial Sequence
<220> FEATURE:
<221> NAME/KEY: MOD_RES
<222> LOCATION: 1
<220> FEATURE:
<221> NAME/KEY: MOD_RES
<222> LOCATION: 6
<220> FEATURE:
<221> NAME/KEY: AMIDATION
<222> LOCATION: 6
<223> OTHER INFORMATION: Designed peptide having PAR-2 agonist activity.
      Xaa at 1 is trans-cynnamoyl-Leu. Xaa at 6 is Orn. The C-terminal
      amino acid residue is amidated.

<400> SEQUENCE: 3

Xaa Ile Gly Arg Leu Xaa
1               5

<210> SEQ ID NO 4
<211> LENGTH: 5
<212> TYPE: PRT
<213> ORGANISM: Artificial Sequence
<220> FEATURE:
<221> NAME/KEY: AMIDATION
<222> LOCATION: 5
<223> OTHER INFORMATION: Designed peptide having PAR-1 and PAR-2 agonist
      activity. The C-terminal amino acid residue is amidated.

<400> SEQUENCE: 4

Ser Phe Leu Leu Arg
1               5

<210> SEQ ID NO 5
<211> LENGTH: 6
<212> TYPE: PRT
<213> ORGANISM: Artificial Sequence
<220> FEATURE:
<221> NAME/KEY: AMIDATION
<222> LOCATION: 6
<223> OTHER INFORMATION: Designed control peptide. The C-terminal amino
      acid residue is amidated.

<400> SEQUENCE: 5

Leu Arg Gly Ile Leu Ser
1               5
```